(12) United States Patent
Marion

(10) Patent No.: US 11,897,608 B2
(45) Date of Patent: Feb. 13, 2024

(54) METHODS, SYSTEMS, APPARATUSES, AND DEVICES FOR FACILITATING SAMPLING WATER OF WATER BODIES

(71) Applicant: Daniel Marion, Vero Beach, FL (US)

(72) Inventor: Daniel Marion, Vero Beach, FL (US)

( * ) Notice: Subject to any disclaimer, the term of this patent is extended or adjusted under 35 U.S.C. 154(b) by 126 days.

(21) Appl. No.: 17/589,399

(22) Filed: Jan. 31, 2022

(65) Prior Publication Data

US 2022/0242561 A1 Aug. 4, 2022

Related U.S. Application Data

(60) Provisional application No. 63/143,341, filed on Jan. 29, 2021.

(51) Int. Cl.
| | |
|---|---|
| *G01N 1/10* | (2006.01) |
| *G01N 33/18* | (2006.01) |
| *G01N 1/12* | (2006.01) |
| *B64C 39/02* | (2023.01) |
| *B64U 101/00* | (2023.01) |

(52) U.S. Cl.
CPC ............ *B64C 39/024* (2013.01); *G01N 1/10* (2013.01); *G01N 33/18* (2013.01); *B64U 2101/00* (2023.01)

(58) Field of Classification Search
CPC ........ B64C 39/024; G01N 1/10; G01N 33/18; G01N 33/1886; G01N 1/12; B64U 2101/00
See application file for complete search history.

(56) References Cited

U.S. PATENT DOCUMENTS

| | | | |
|---|---|---|---|
| 9,963,228 B2 | 5/2018 | McCullough | |
| 2004/0004545 A1* | 1/2004 | Early | G01F 23/64 340/539.26 |
| 2017/0329351 A1 | 11/2017 | Park | |
| 2018/0279594 A1 | 10/2018 | Raskas | |
| 2019/0310236 A1* | 10/2019 | Scott | G01N 33/18 |
| 2020/0393333 A1* | 12/2020 | Cheng | G01N 1/10 |

FOREIGN PATENT DOCUMENTS

| | | | | |
|---|---|---|---|---|
| CN | 207379763 U | | 5/2018 | |
| GB | 2196202 A | * | 4/1988 | ............. G01N 27/07 |
| JP | 6235716 B2 | | 1/2017 | |

* cited by examiner

*Primary Examiner* — Herbert K Roberts
*Assistant Examiner* — Anthony W Megna Fuentes

(57) ABSTRACT

Disclosed herein is an apparatus for facilitating sampling water of water bodies, in accordance with some embodiments. Further, the apparatus comprises a primary housing, a secondary housing, a movement assembly, a sensor, a storage device, and a power source. Further, the secondary housing is submerged in a water body based on disposing of the primary housing. Further, the secondary housing receives a water sample from a depth of the water body in a secondary interior cavity through an opening of the secondary housing based on submerging of the secondary housing in the water body in the depth. Further, the movement assembly transitions the secondary housing between a retracted position and an extended position for the submerging. Further, the sensor generates sensor data based on detecting a characteristic of the water sample. Further, the storage device stores the sensor data. Further, the power source powers the sensor, and the storage device.

14 Claims, 17 Drawing Sheets

METHODS, SYSTEMS, APPARATUSES, AND DEVICES FOR FACILITATING SAMPLING WATER OF WATER BODIES

The current application claims a priority to the U.S. provisional patent application Ser. No. 63/143,341 filed on Jan. 29, 2021. The current application is filed on Jan. 31, 2022 while Jan. 29, 2022 was on a weekend.

FIELD OF THE INVENTION

Generally, the present disclosure relates to the field of measuring and testing. More specifically, the present disclosure relates to methods, systems, apparatuses, and devices for facilitating sampling water of water bodies.

BACKGROUND OF THE INVENTION

Sampling water from water bodies, particularly large and deep ones is difficult to get a sample from. Water sample and testing is an important task to ensure the safety of marine life and of human beings.

Existing techniques for sampling water of water bodies are deficient with regard to several aspects. For instance, current technologies do not use drones to remotely travel to water bodies. Furthermore, current technologies do not provide a detachable component that penetrates deep inside the water for sampling the water. Moreover, current technologies are not waterproof.

Therefore, there is a need for improved methods, systems, apparatuses, and devices for facilitating sampling water of water bodies that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is an apparatus for facilitating sampling water of water bodies, in accordance with some embodiments. Further, the apparatus may be disposable on a water surface of the water bodies. Further, the apparatus may include a primary housing, a secondary housing, a movement assembly, at least one sensor, a storage device, and at least one power source. Further, the primary housing may include a primary interior cavity. Further, the primary housing may be disposable on at least one water surface of at least one water body. Further, the secondary housing may be movably disposed on a lower portion of the primary housing. Further, the secondary housing may be submerged in the at least one water body based on disposing of the primary housing on the at least one water surface. Further, the secondary housing may include a secondary interior cavity and at least one opening leading into the secondary interior cavity. Further, the secondary housing may be transitionable between a retracted position and at least one extended position. Further, the secondary housing may be configured for receiving at least one water sample from at least one depth of the at least one water body in the secondary interior cavity through the at least one opening based on submerging of the secondary housing in the at least one water body in the at least one depth. Further, the submerging of the secondary housing in the at least one depth may be based on transitioning of the secondary housing from the retracted position to the at least one extended position. Further, the movement assembly may be disposed in the primary interior cavity of the primary housing. Further, the movement assembly may be operationally coupled with the secondary housing. Further, the movement assembly may be configured for transitioning the secondary housing between the retracted position and the at least one extended position. Further, the movement assembly may include at least one actuator and at least one tether. Further, a first end of the at least one tether may be coupled with the at least one actuator and a second end of the at least one tether may be coupled with the secondary housing. Further, the at least one actuator may be configured for transitioning the at least one tether between a retracted state and at least one extended state. Further, the transitioning of the secondary housing between the retracted position and the at least one extended position may be based on the transitioning the at least one tether between the retracted state and the at least one extended state. Further, the at least one sensor may be disposed in the secondary interior cavity. Further, the at least one sensor may be configured for generating at least one sensor data based on detecting at least one characteristic of the at least one water sample received in the secondary interior cavity. Further, the storage device may be disposed in the primary interior cavity. Further, the storage device may be communicatively coupled with the at least one sensor. Further, the storage device may be configured for storing the at least one sensor data. Further, the at least one power source may be disposed in the primary interior cavity. Further, the at least one power source may be electrically coupled with the at least one actuator, the at least one sensor, and the storage device. Further, the at least one power source may be configured for powering the at least one actuator, the at least one sensor, and the storage device.

Further disclosed herein is an apparatus for facilitating sampling water of water bodies, in accordance with some embodiments. Further, the apparatus may be disposable on a water surface of the water bodies. Further, the apparatus may include a primary housing, a secondary housing, a movement assembly, at least one sensor, a storage device, a processing device, and at least one power source. Further, the primary housing may include a primary interior cavity. Further, the primary housing may be disposable on at least one water surface of at least one water body. Further, the secondary housing may be movably disposed on a lower portion of the primary housing. Further, the secondary housing may be submerged in the at least one water body based on disposing of the primary housing on the at least one water surface. Further, the secondary housing may include a secondary interior cavity and at least one opening leading into the secondary interior cavity. Further, the secondary housing may be transitionable between a retracted position and at least one extended position. Further, the secondary housing may be configured for receiving at least one water sample from at least one depth of the at least one water body in the secondary interior cavity through the at least one opening based on submerging of the secondary housing in the at least one water body in the at least one depth. Further, the submerging of the secondary housing in the at least one depth may be based on transitioning of the secondary housing from the retracted position to the at least one extended position. Further, the movement assembly may be disposed in the primary interior cavity of the primary housing. Further, the movement assembly may be operationally coupled with the secondary housing. Further, the movement assembly may be configured for transitioning the secondary housing between the retracted position and the at least one extended position. Further, the movement assembly may include at least one actuator and at least one tether. Further, a first end of the at least one tether may be coupled with the at least one actuator and a second end of the at least one tether may be coupled with the secondary housing. Further, the at least one actuator may be configured for transitioning the at least one tether between a retracted state and at least one extended state. Further, the transitioning of the secondary housing between the retracted position and the at least one extended position may be based on the transitioning the at least one tether between the retracted state and the at least one extended state. Further, the at least one sensor may be disposed in the secondary interior cavity. Further, the at least one sensor may be configured for generating at least one sensor data based on detecting at least one characteristic of the at least one water sample received in the secondary interior cavity. Further, the storage device may be disposed in the primary interior cavity. Further, the storage device may be communicatively coupled with the at least one sensor. Further, the storage device may be configured for storing the at least one sensor data. Further, the processing device may be disposed in the primary interior cavity. Further, the processing device may be communicatively coupled with the at least one actuator. Further, the processing device may be configured for analyzing at least one operational data. Further, the processing device may be configured for generating at least one command based on the analyzing of the at least one operational data. Further, the transitioning of the at least one tether between the retracted state and the at least one extended state may be based on the at least one command. Further, the at least one power source may be disposed in the primary interior cavity. Further, the at least one power source may be electrically coupled with the at least one actuator, the at least one sensor, the storage device, and the processing device. Further, the at least one power source may be configured for powering the at least one actuator, the at least one sensor, the storage device, and the processing device.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

Figure 1:
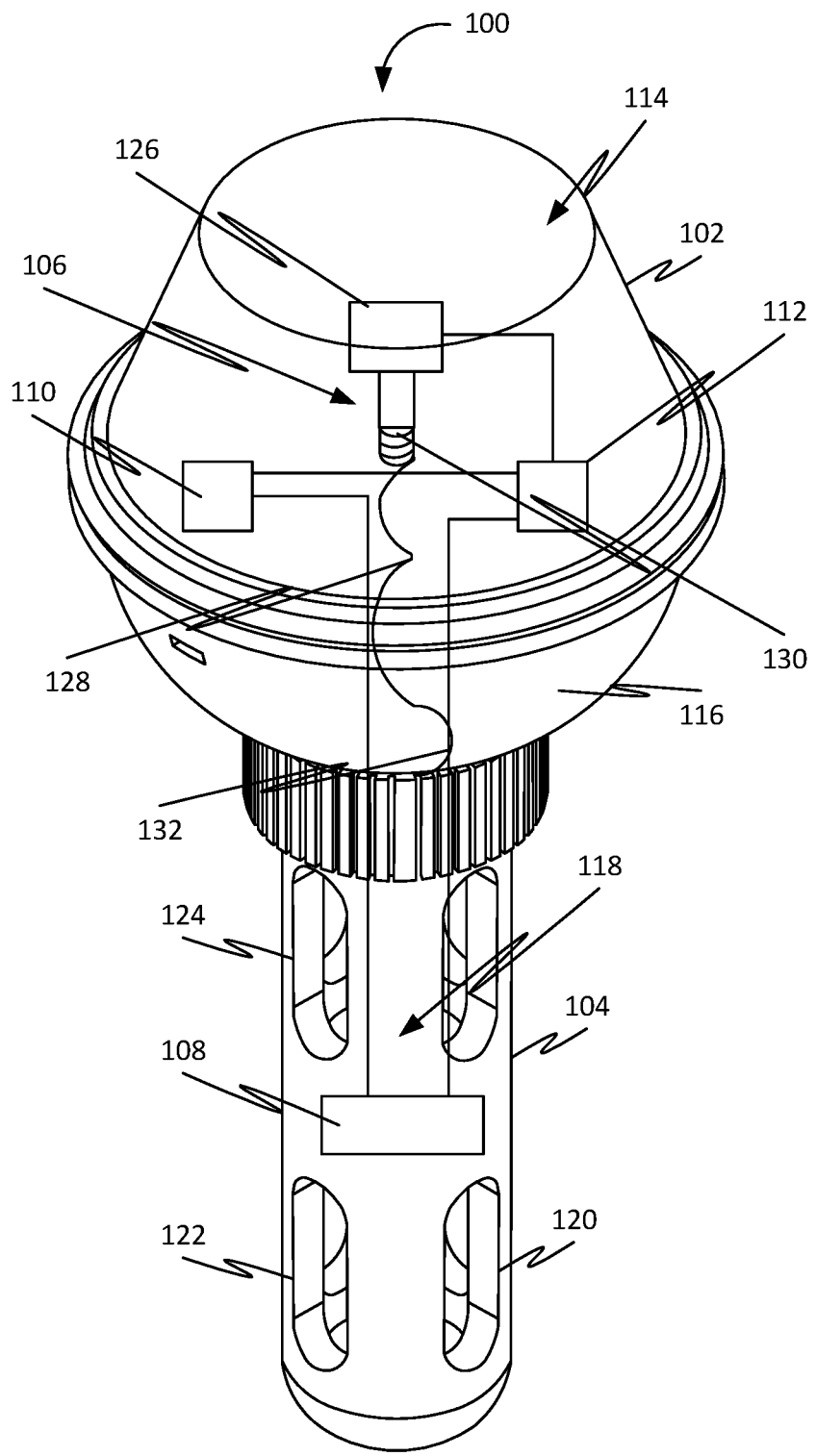
FIG. 1 is a top front perspective view of an apparatus for facilitating sampling water of water bodies, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods, systems, apparatuses, and devices for facilitating sampling water of water bodies, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g., a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g., Windows, Mac OS, Unix, Linux, Android, etc.) in order to provide a user interface (e.g., GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g., username, password, passphrase, PIN, secret question, secret answer etc.) and/or possession of a machine readable secret data (e.g., encryption key, decryption key, bar codes, etc.) and/or or possession of one or more embodied characteristics unique to the user (e.g., biometric variables such as, but not limited to, fingerprint, palm-print, voice characteristics, behavioral characteristics, facial features, iris pattern, heart rate variability, evoked potentials, brain waves, and so on) and/or possession of a unique device (e.g., a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g., transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g., the server computer, a client device etc.) corresponding to the performance of the one or more steps, environmental variables (e.g., temperature, humidity, pressure, wind speed, lighting, sound, etc.) associated with a device corresponding to the performance of the one or more steps, physical state and/or physiological state and/or psychological state of the user, physical state (e.g., motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g., a real-time clock), a location sensor (e.g., a GPS receiver, a GLONASS receiver, an indoor location sensor etc.), a biometric sensor (e.g., a fingerprint sensor), an environmental variable sensor (e.g., temperature sensor, humidity sensor, pressure sensor, etc.) and a device state sensor (e.g., a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g., initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview

The present disclosure describes methods, systems, apparatuses, and devices for facilitating sampling water of water bodies.

Further, the present disclosure describes an apparatus that aids in water sampling in any type of water body. The disclosed apparatus uses drones to remotely travel to water bodies and collect a sample. Additionally, the disclosed apparatus has a detachable component that penetrates deep inside the water body in order to collect a water sample. Further, the disclosed apparatus is completely waterproof, preventing the disclosed apparatus from any water damage. Additionally, the disclosed apparatus operates even when the drone is shut off. The drone lands on the water surface while the disclosed apparatus is submerged underwater. In this process, the drone can be shut down while the user collects data without running out of battery life. This allows the disclosed apparatus to operate for as long as possible or as long as the user needs to collect data from the disclosed apparatus. Further, the disclosed apparatus may be an aqua data pod. Further, the aqua data pod is an attachment for a drone. More specifically, the aqua data pod is a waterproof device that connects to a waterproof drone. Additionally, the disclosed apparatus is used to collect a water sample from any feasible water body. The aqua data pod comprises a first housing, a disc, a cord, a second housing, a third housing, and a controller. Further, the first housing is the topmost piece of the aqua data pod. More specifically, the aqua data pod acts as a shield for the top portion of the aqua data pod. Moreover, the first housing serves as a shield for the circuit board and the connectivity of the controller. In the preferred embodiment of the disclosed apparatus, the first housing is a hollow cap-like structure but can be of any other viable shape or form.

The first housing comprises a connection ring, a first screen, a first ring, and a rubber seal. Further, the connection ring resides on the topmost surface of the first housing. More specifically, the connection ring serves as a connection point that connects to the contact pins of the drone. Furthermore, the signal from the sensors travels from the circuit to the connection rings to the contact pins of the drone. The drone can further transfer the data through the connectivity of the controller. Further, the first screen is the sidewall for the first housing. Additionally, the first ring is adjacent to the connection ring. More specifically, the first screen serves as a shield for the controller's circuit board. Further, the first ring is adjacent to the first screen. Moreover, the first ring protrudes out of the first screen. More specifically, the first ring serves as a platform for the rubber seal. Further, the rubber seal resides on the first ring. More specifically, the rubber seal protects the connection ring from being damaged by water. Further, the disc is a separation plate. Additionally, the disc resides inside the first housing and the second housing. Moreover, the disc is concentrically aligned with the first housing. More specifically, the disc seals the circuit board of the controller in the first housing to keep the controller protected from water damage. Further, the cord traverses from the second housing to the third housing of the aqua data pod. Additionally, the cord begins at the motor and traverses all the way to the sensor of the controller. More specifically, the cord can be wind and unwind allowing the third housing to submerge deep inside the water to collect data. Further, the second housing is adjacent to the first housing. Additionally, the second housing is concentrically aligned to the first housing of the aqua data pod. Furthermore, the second housing completes the first housing from the lower portion making the structure sealed. More specifically, the second housing serves as a shield for the motor and the cord while protecting the motor and the cord from water damage. Moreover, the outer surface of the second housing serves as a platform for the connector, the spotlights, and the manual setting of the controller. In the preferred embodiment of the disclosed apparatus, the second housing is a hollow bowl structure but is not limited to this. Further, the third housing is adjacent to the second housing. Additionally, the third housing is concentrically aligned with the second housing. Moreover, the third housing can detach from the second housing and drop down deeper into the water to collect the water sample. Furthermore, the third housing can be retrieved by using the cord. More specifically, the third housing serves as a protective cover for the sensors. The third housing comprises a plurality of apertures. Further, the plurality of apertures are cutouts that reside on the third housing. Additionally, the plurality of apertures is circularly patterned around the third housing. More specifically, the plurality of apertures allows the water to get inside for the sensor to collect data. Further, the controller resides on the aqua data pod. More specifically, the controller controls the data transfer, power supply, and the third housing of the aqua data pod. The controller comprises a power supply, a connectivity, a motor, a first connector, a second connector, a manual setting, a plurality of spotlights, and a sensor. Further, the power supply serves as a unit that supplies power to the controller. In the preferred embodiment of the disclosed apparatus, the power supply is a lithium rechargeable battery but not limited to this type only. Further, the connectivity is part of the controller which allows the user to control the aqua data pod and transfer data from the aqua data pod to a storage device. Further, the motor resides in the second housing of the aqua data pod. More specifically, the motor serves as a mechanism for lowering and retracting the cord of the aqua data pod. Moreover, the motor is waterproof. Further, the first connector is a connection mechanism through which the aqua data pod can be connected to another device. Additionally, the first connector resides on the second housing. In the preferred embodiment of the disclosed apparatus, the first connector is a USB port. More specifically, the first connector serves as a charging port and as a data downloading medium. Moreover, the first connector acts as an on and off switch to turn the disclosed apparatus on or off by completing the circuit. In the preferred embodiment of the disclosed apparatus, the first connector completes the circuit when the first connector is touched by water. Further, the second connector is a wireless connection mechanism. In the preferred embodiment of the disclosed apparatus, the second connector is used to transfer data through wireless connectivity. Further, the manual setting resides on the second housing. Additionally, the manual setting can be operated when a remote operation is unavailable. Moreover, the manual setting has different sets of buttons that can be used to control the disclosed apparatus and also to collect and download data. Further, the plurality of spotlights resides on the second housing. Additionally, the plurality of spotlights is for night-time maneuvering. More specifically, the plurality of spotlights is used for lighting for remote operation. Further, the sensor resides inside the third housing. More specifically, the sensor is used to sense water samples.

Further, the present disclosure relates generally to an apparatus for a water-proof drone. More specifically, the disclosed apparatus is an attachment for a drone that allows collecting water samples from the water body.

FIG. 1 is a top front perspective view of an apparatus 100 for facilitating sampling water of water bodies, in accordance with some embodiments. Further, the apparatus 100 may be disposable on a water surface of the water bodies. Further, the apparatus 100 may include a primary housing 102, a secondary housing 104, a movement assembly 106, at least one sensor 108, a storage device 110, and at least one power source 112. Further, the apparatus 100 may be waterproof.

Further, the primary housing 102 may include a primary interior cavity 114. Further, the primary housing 102 may be disposable on at least one water surface of at least one water body.

Further, the secondary housing 104 may be movably disposed on a lower portion 116 of the primary housing 102. Further, the secondary housing 104 may be submerged in the at least one water body based on disposing of the primary housing 102 on the at least one water surface. Further, the secondary housing 104 may include a secondary interior cavity 118 and at least one opening 120-124 leading into the secondary interior cavity 118. Further, the secondary housing 104 may be transitionable between a retracted position and at least one extended position. Further, the secondary housing 104 may be configured for receiving at least one water sample from at least one depth of the at least one water body in the secondary interior cavity 118 through the at least one opening 120-124 based on submerging of the secondary housing 104 in the at least one water body in the at least one depth. Further, the submerging of the secondary housing 104 in the at least one depth may be based on transitioning of the secondary housing 104 from the retracted position to the at least one extended position.

Further, the movement assembly 106 may be disposed in the primary interior cavity 114 of the primary housing 102. Further, the movement assembly 106 may be operationally coupled with the secondary housing 104. Further, the movement assembly 106 may be configured for transitioning the secondary housing 104 between the retracted position and the at least one extended position. Further, the movement assembly 106 may include at least one actuator 126 and at least one tether 128. Further, the at least one tether 128 may include a cord. Further, a first end 130 of the at least one tether 128 may be coupled with the at least one actuator 126 and a second end 132 of the at least one tether 128 may be coupled with the secondary housing 104. Further, the at least one actuator 126 may be configured for transitioning the at least one tether 128 between a retracted state and at least one extended state. Further, the transitioning of the secondary housing 104 between the retracted position and the at least one extended position may be based on the transitioning the at least one tether 128 between the retracted state and the at least one extended state.

Further, the at least one sensor 108 may be disposed in the secondary interior cavity 118. Further, the at least one sensor 108 may be configured for generating at least one sensor data based on detecting at least one characteristic of the at least one water sample received in the secondary interior cavity 118. Further, the at least one characteristic may include at least one water quality characteristic. Further, the at least one water quality characteristic may include stream flow, dissolved oxygen and biochemical oxygen demand, temperature, pH, turbidity, phosphorus, nitrates, total solids, conductivity, total alkalinity, fecal bacteria, conductivity, odor, sediment, turbidity, bioindicators, etc.

Further, the storage device 110 may be disposed in the primary interior cavity 114. Further, the storage device 110 may be communicatively coupled with the at least one sensor 108. Further, the storage device 110 may be configured for storing the at least one sensor data. Further, the at least one power source 112 may be disposed in the primary interior cavity 114.

Further, the at least one power source 112 may be electrically coupled with the at least one actuator 126, the at least one sensor 108, and the storage device 110. Further, the at least one power source 112 may include at least one battery. Further, the at least one power source 112 may be configured for powering the at least one actuator 126, the at least one sensor 108, and the storage device 110.

Further, in some embodiments, the primary housing 102 may be watertight.

In further embodiments, the apparatus 100 may include a processing device 202 disposed in the primary interior cavity 114. Further, the processing device 202 may be electrically coupled with the at least one power source 112. Further, the at least one power source 112 may be further configured for powering the processing device 202. Further, the processing device 202 may be communicatively coupled with the at least one actuator 126. Further, the processing device 202 may be configured for analyzing at least one operational data. Further, the at least one operational data may include at least one operational instruction for operating the apparatus 100. Further, the processing device 202 may be configured for generating at least one command based on the analyzing of the at least one operational data. Further, the transitioning of the at least one tether 128 between the retracted state and the at least one extended state may be based on the at least one command.

Further, in an embodiment, the storage device 110 may be configured for storing the at least one operational data.

In an embodiment, the apparatus 100 may include a communication device 302 disposed in the primary interior cavity 114. Further, the communication device 302 may be electrically coupled with the at least one power source 112. Further, the at least one power source 112 may be further configured for powering the communication device 302. Further, the communication device 302 may be communicatively coupled with the processing device 202. Further, the communication device 302 may be further configured for receiving the at least one operational data from at least one user device 304.

In further embodiments, the apparatus 100 may include a communication device 402 disposed in the primary interior cavity 114. Further, the communication device 402 may be electrically coupled with the at least one power source 112. Further, the at least one power source 112 may be further configured for powering the communication device 402. Further, the communication device 402 may be communicatively coupled with the storage device 110. Further, the communication device 402 may be configured for transmitting the at least one sensor data to at least one user device 404.

Further, in some embodiments, the at least one actuator 126 may include a motor 502. Further, the movement assembly 106 further may include a wounding member 504. Further, a shaft 506 of the motor 502 may be mechanically coupled with a first end 508 of the wounding member 504. Further, the at least one tether 128 may be unwoundably woundable on the wounding member 504. Further, the motor 502 may be configured for rotating the wounding member 504 in at least one of a clockwise direction and an anti-clockwise direction about a longitudinal axis of the wounding member 504 for unwoundingly wounding the at least one tether 128 on the wounding member 504. Further, the transitioning of the at least one tether 128 between the retracted state and the at least one extended state may be based on the unwoundingly wounding the at least one tether 128 on the wounding member 504.

In further embodiments, the apparatus 100 may include at least one connection element 602 disposed on a top portion 604 of the primary housing 102. Further, the at least one connection element 602 may include at least one first fastener. Further, the at least one connection element 602 may be configured to be detachably attachable to at least one drone connection element 702 of at least one drone 700 for detachably attaching the apparatus 100 to the at least one drone 700. Further, the at least one drone connection element 702 may include at least one second fastener. Further, the at least one first fastener and the at least one second fastener may be detachably attachable. Further, the at least one drone 700 disposes the apparatus 100 on the water surface.

Further, in an embodiment, the at least one drone 700 maneuvers the apparatus 100 on the water surface of the water bodies based on attaching of the apparatus 100 to the at least one drone 700.

In an embodiment, the apparatus 100 may include at least one lighting device 802 disposed on the primary housing 102. Further, the at least one lighting device 802 may include a spotlight. Further, the at least one lighting device 802 may be electrically coupled with the at least one power source 112. Further, the at least one power source 112 may be further configured for powering the at least one lighting device 802. Further, the at least one lighting device 802 may be configured for illuminating at least a portion of the water bodies. Further, the illuminating facilitates maneuvering of the apparatus 100.

Further, in an embodiment, the illuminating further may include illuminating the at least one water sample. Further, the detecting of the at least one characteristic may be further based on the illuminating of the at least one water sample.

In further embodiments, the apparatus 100 may include at least one communication interface 902 disposed in the primary interior cavity 114. Further, the at least one communication interface 902 may include a USB port, etc. Further, the at least one communication interface 902 may be communicatively coupled with the storage device 110. Further, the at least one communication interface 902 may be configured for establishing a connection between the apparatus 100 and at least one device 904. Further, the establishing of the connection allows transferring of the at least one sensor data from the storage device 110 to the at least one device 904.

Further, in some embodiments, the primary housing 102 may be configured to be flotably disposed on the at least one water surface of the at least one water body.

In further embodiments, the apparatus 100 may include at least one activation sensor 1002 disposed on the primary housing 102. Further, the at least one activation sensor 1002 may be coupled with the at least one power source 112. Further, the at least one activation sensor 1002 may be configured for generating at least one activation signal based on detecting disposing of the apparatus 100 on the water surface of the water bodies. Further, the detecting of the disposing of the apparatus 100 on the water surface of the water bodies may include detecting a presence of water. Further, the powering of the at least one actuator 126, the at least one sensor 108, and the storage device 110 may be further based on the at least one activation signal.

Figure 2:
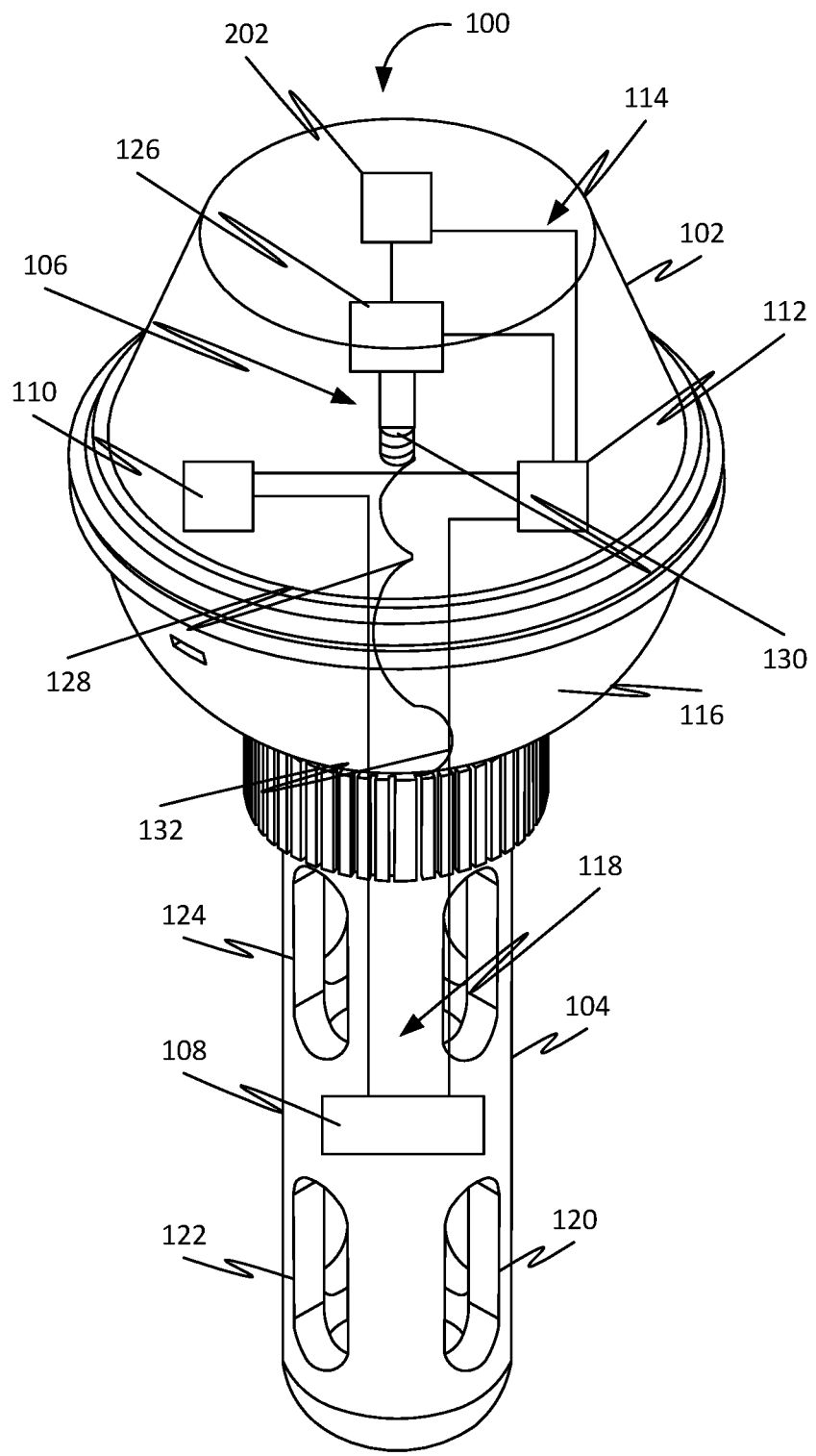
FIG. 2 is a top front perspective view of the apparatus, in accordance with some embodiments.

FIG. 2 is a top front perspective view of the apparatus 100, in accordance with some embodiments.

Figure 3:
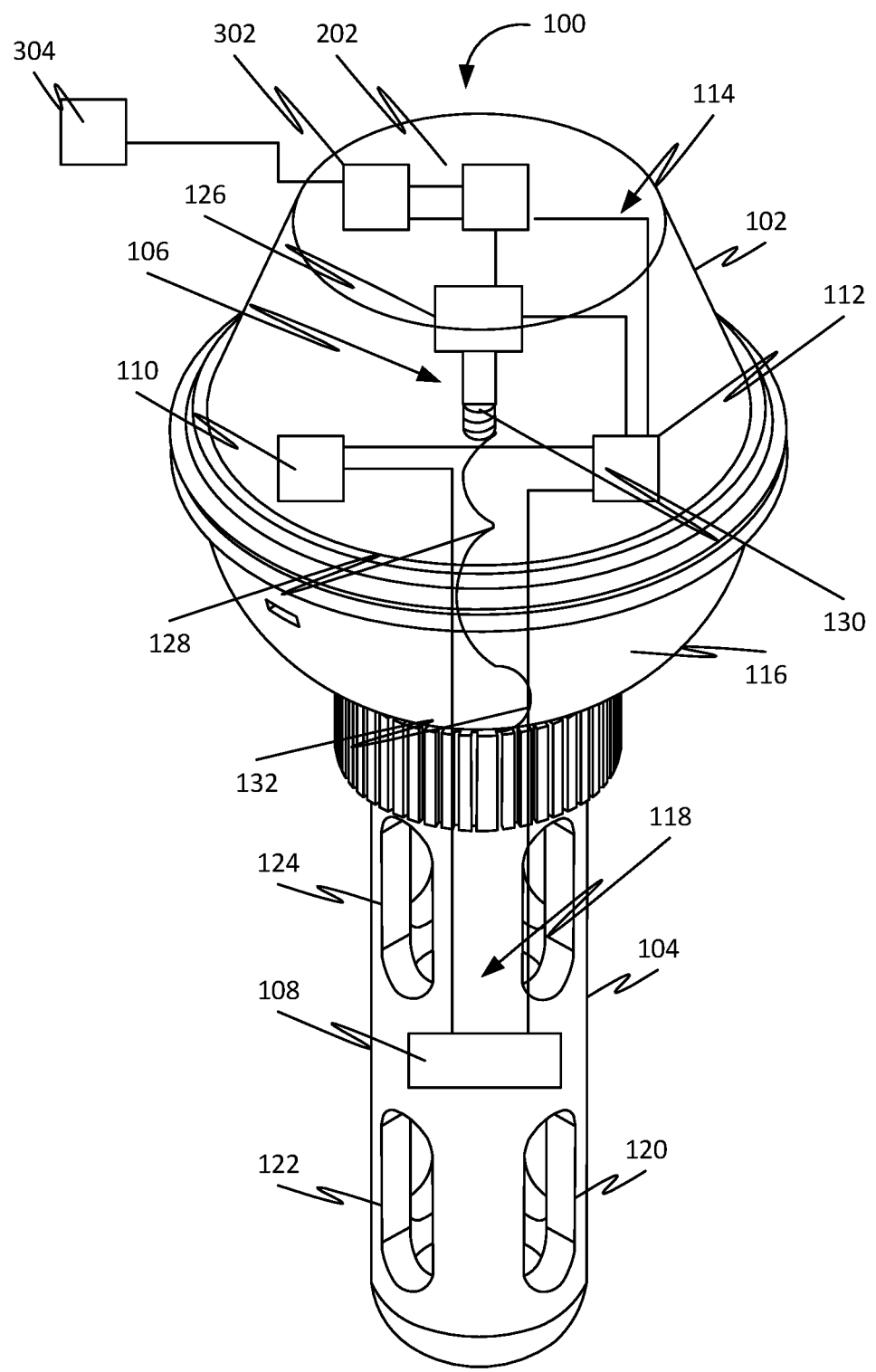
FIG. 3 is a top front perspective view of the apparatus, in accordance with some embodiments.

FIG. 3 is a top front perspective view of the apparatus 100, in accordance with some embodiments.

Figure 4:
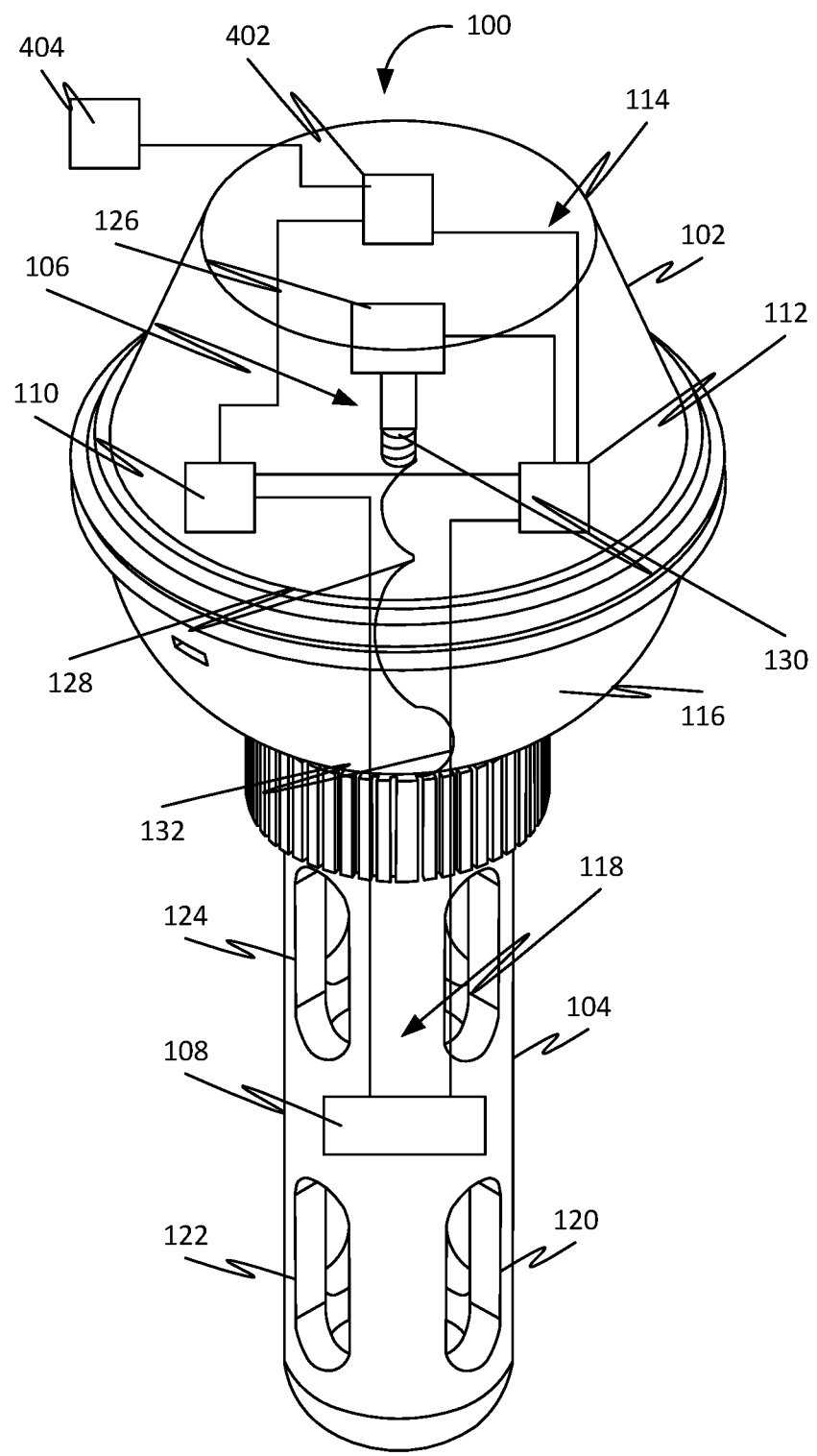
FIG. 4 is a top front perspective view of the apparatus, in accordance with some embodiments.

FIG. 4 is a top front perspective view of the apparatus 100, in accordance with some embodiments.

Figure 5:
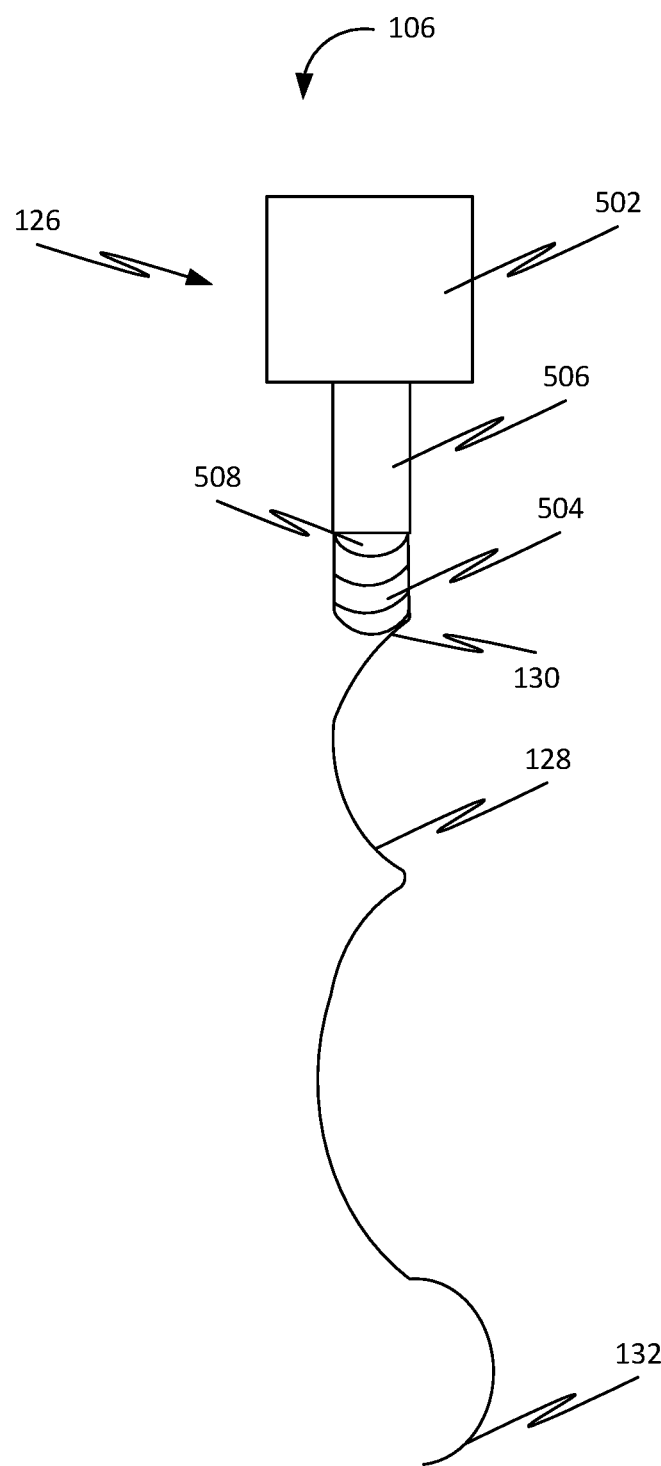
FIG. 5 is a front view of the movement assembly of the apparatus, in accordance with some embodiments.

FIG. 5 is a front view of the movement assembly 106 of the apparatus 100, in accordance with some embodiments.

Figure 6:
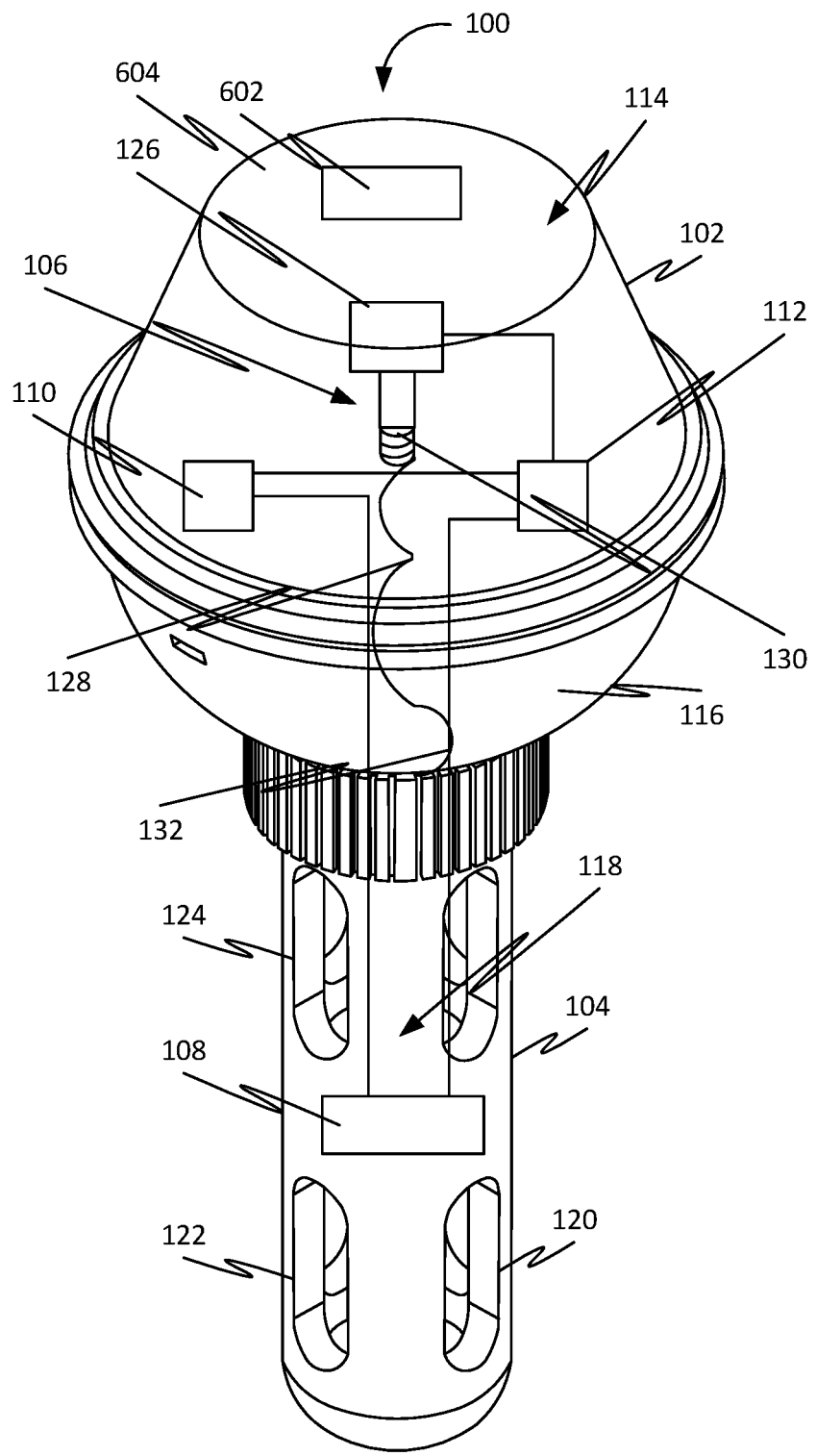
FIG. 6 is a top front perspective view of the apparatus, in accordance with some embodiments.

FIG. 6 is a top front perspective view of the apparatus 100, in accordance with some embodiments.

Figure 7:
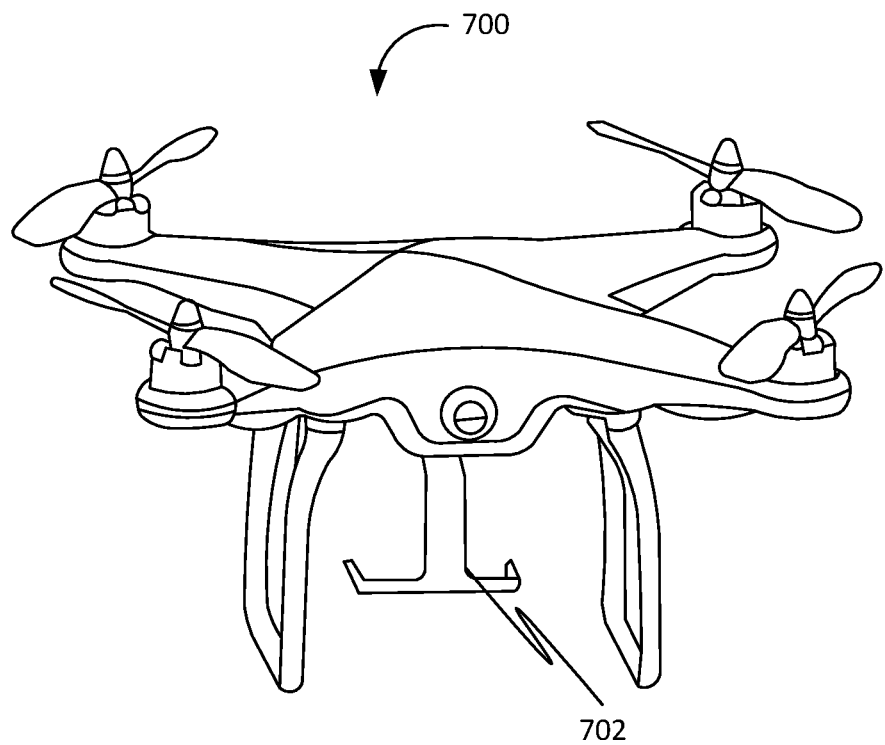
FIG. 7 is a front perspective view of the at least one drone associated with the apparatus, in accordance with some embodiments.

FIG. 7 is a front perspective view of the at least one drone 700 associated with the apparatus 100, in accordance with some embodiments.

Figure 8:
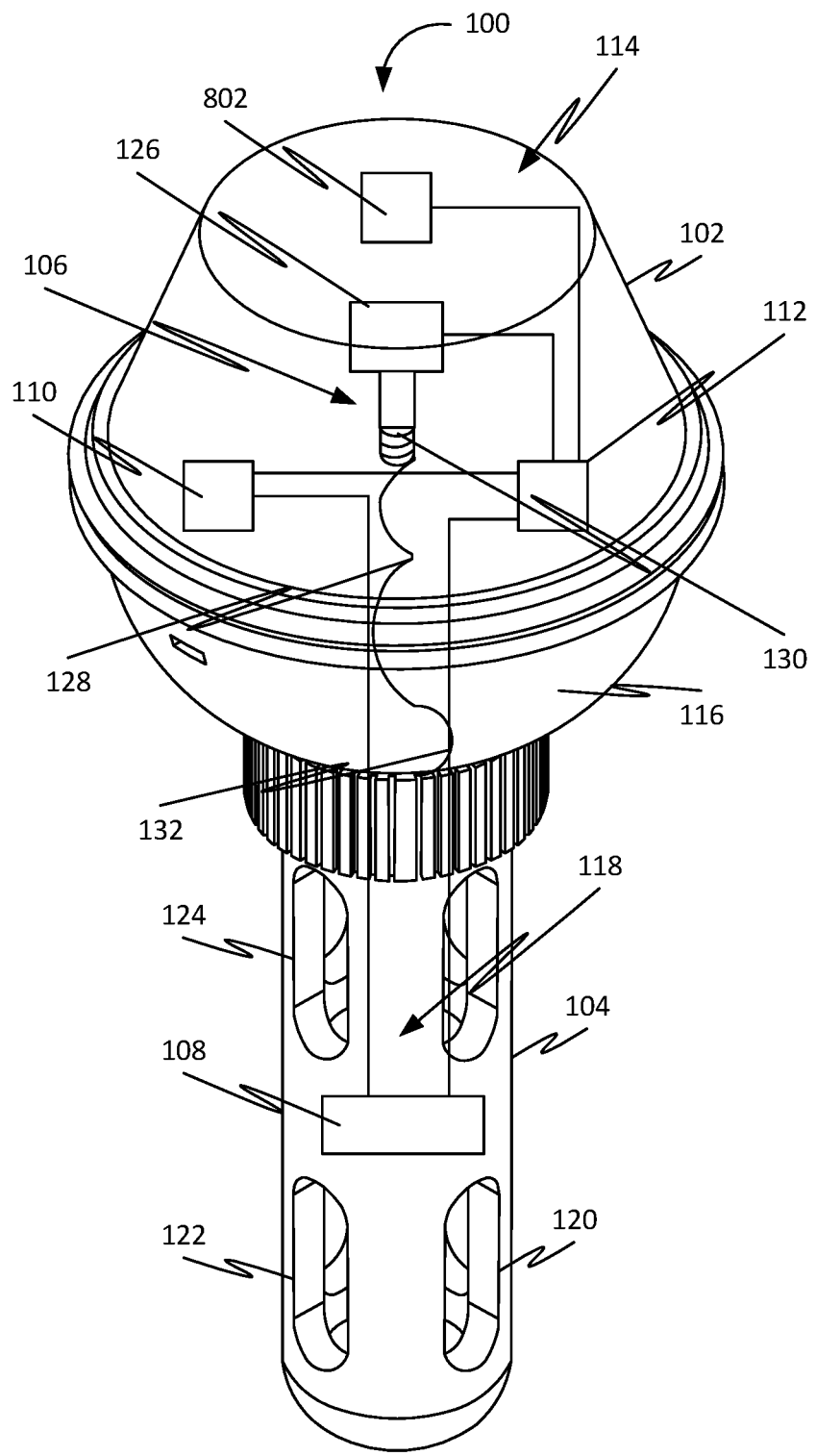
FIG. 8 is a top front perspective view of the apparatus, in accordance with some embodiments.

FIG. 8 is a top front perspective view of the apparatus 100, in accordance with some embodiments.

Figure 9:
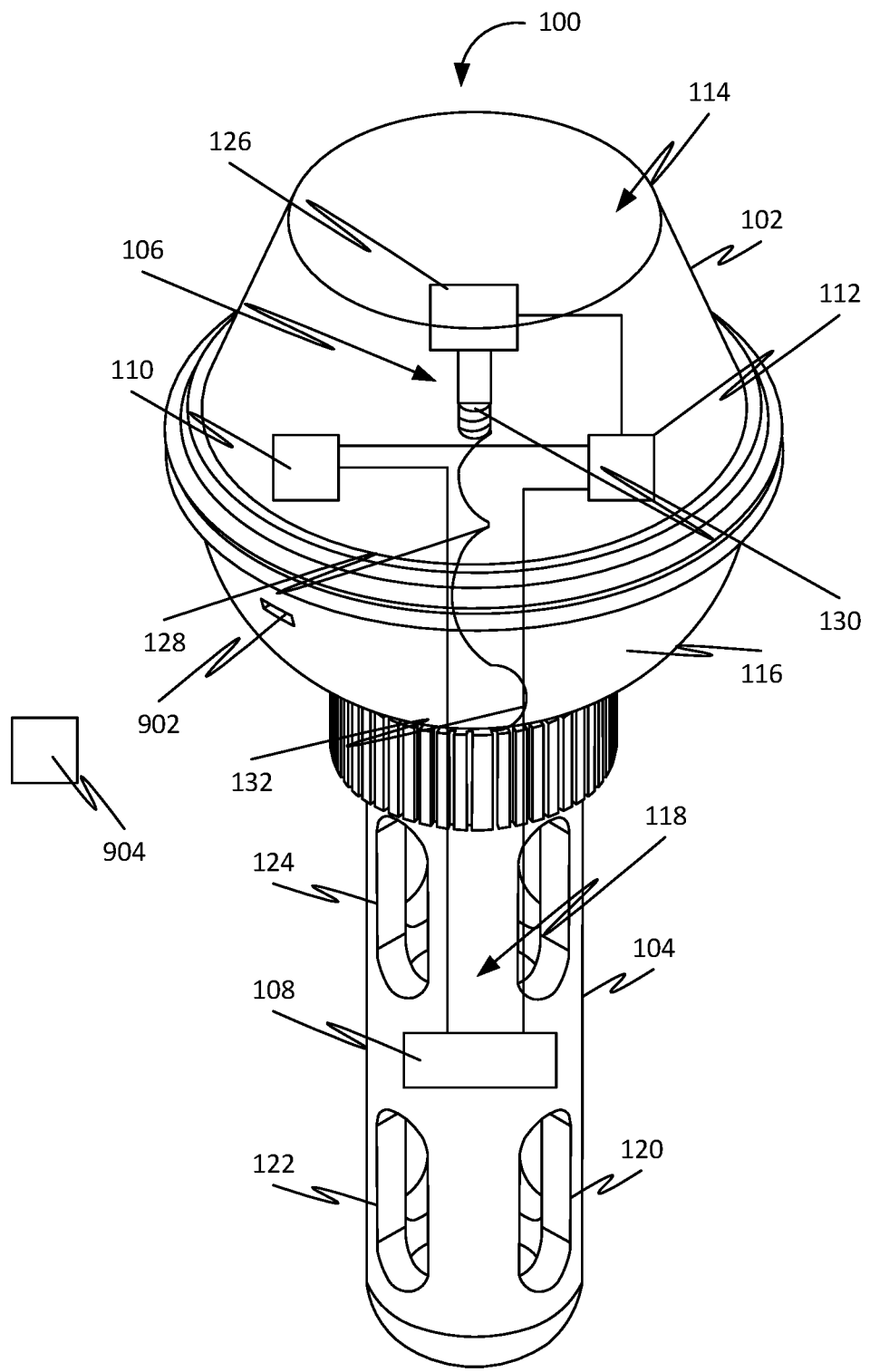
FIG. 9 is a top front perspective view of the apparatus, in accordance with some embodiments.

FIG. 9 is a top front perspective view of the apparatus 100, in accordance with some embodiments.

Figure 10:
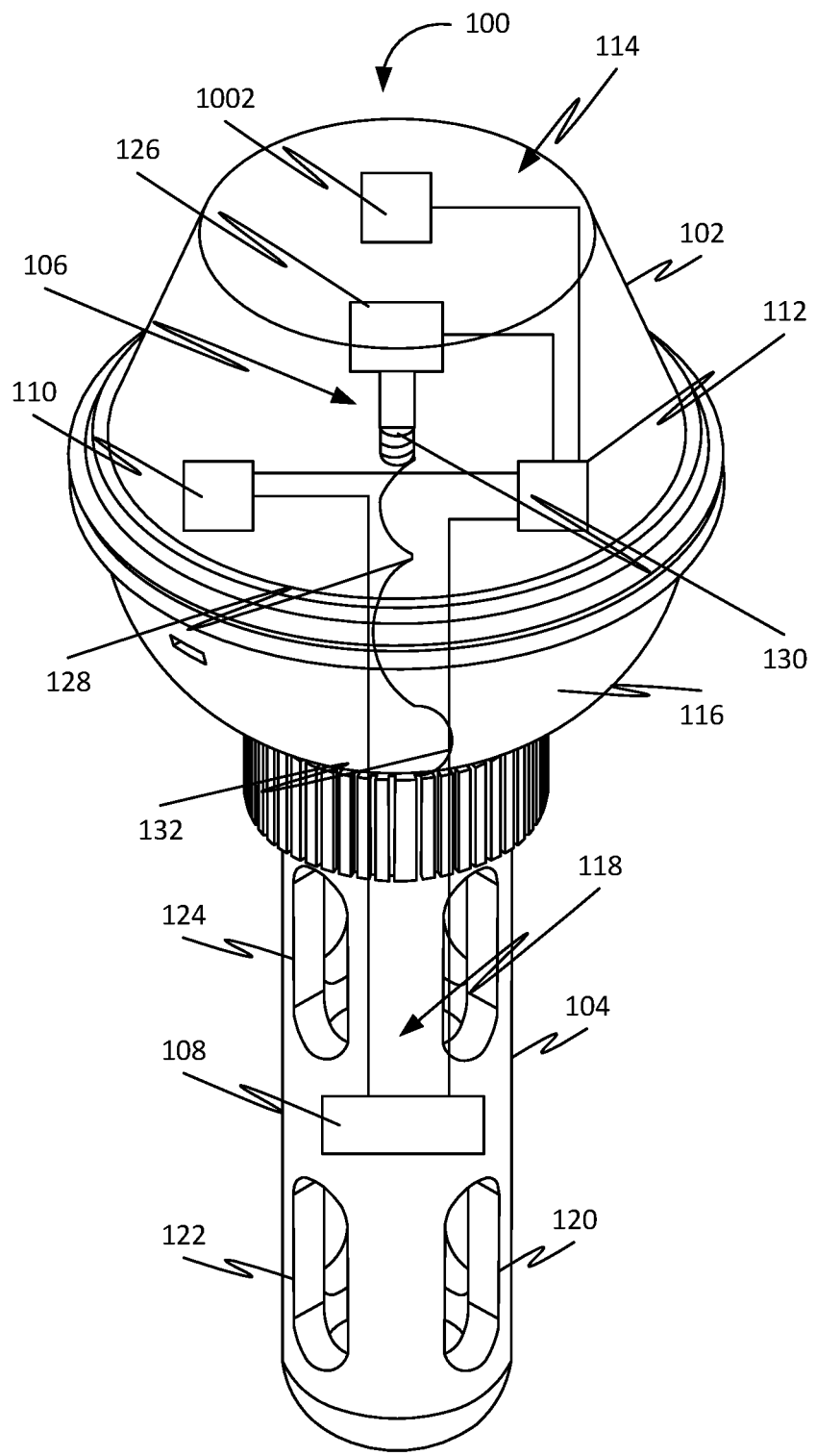
FIG. 10 is a front perspective view of the apparatus, in accordance with some embodiments.

FIG. 10 is a front perspective view of the apparatus 100, in accordance with some embodiments.

Figure 11:
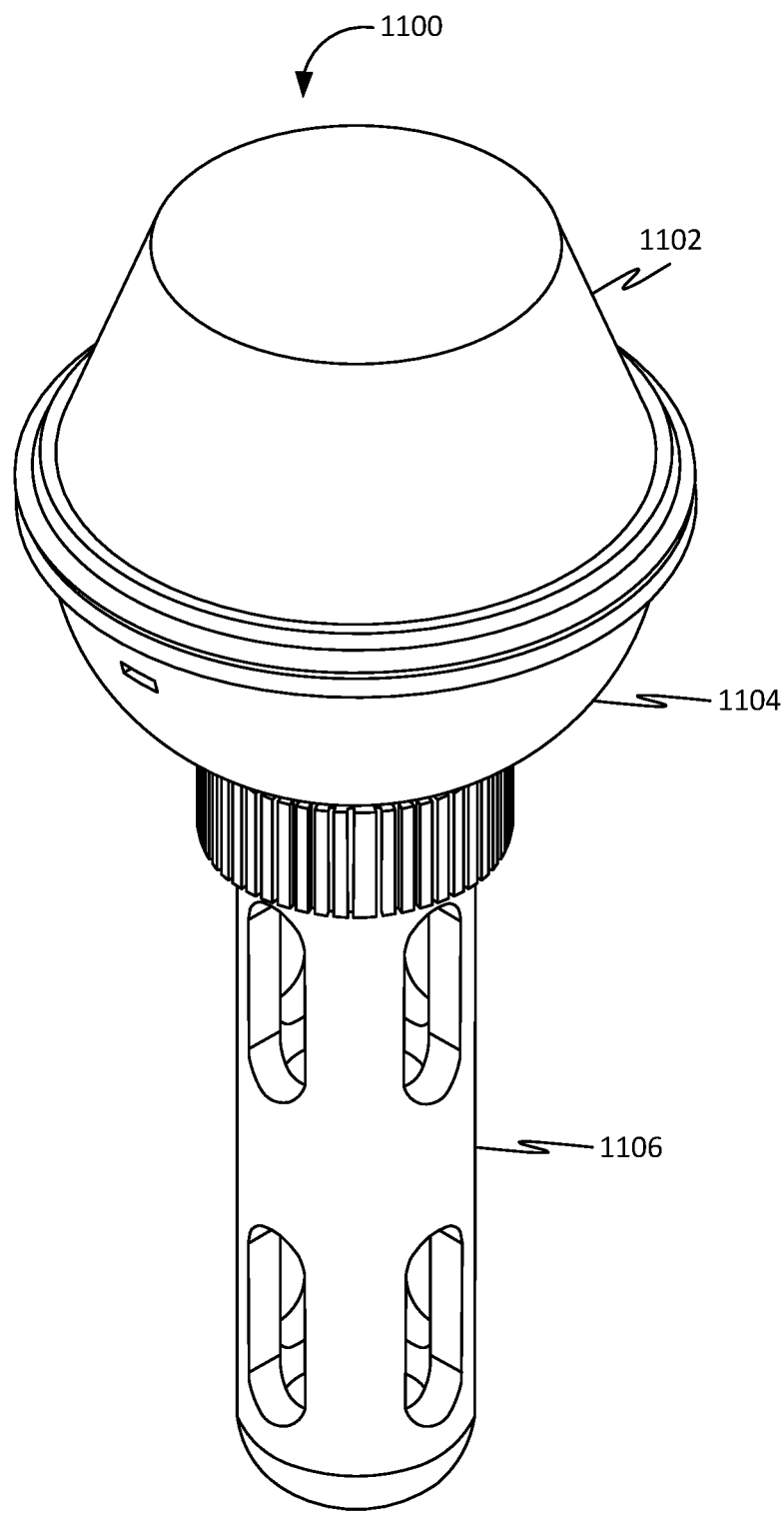
FIG. 11 is a top front perspective view of an apparatus for facilitating sampling water of water bodies, in accordance with some embodiments.

FIG. 11 is a top front perspective view of an apparatus 1100 for facilitating sampling water of water bodies, in accordance with some embodiments. Further, the apparatus 1000 may include a first housing 1102, a second housing 1104, and a third housing 1106. Further, the apparatus 1100 may include a separation plate 1302, a motor 1304, and a cord 1306

Figure 12:
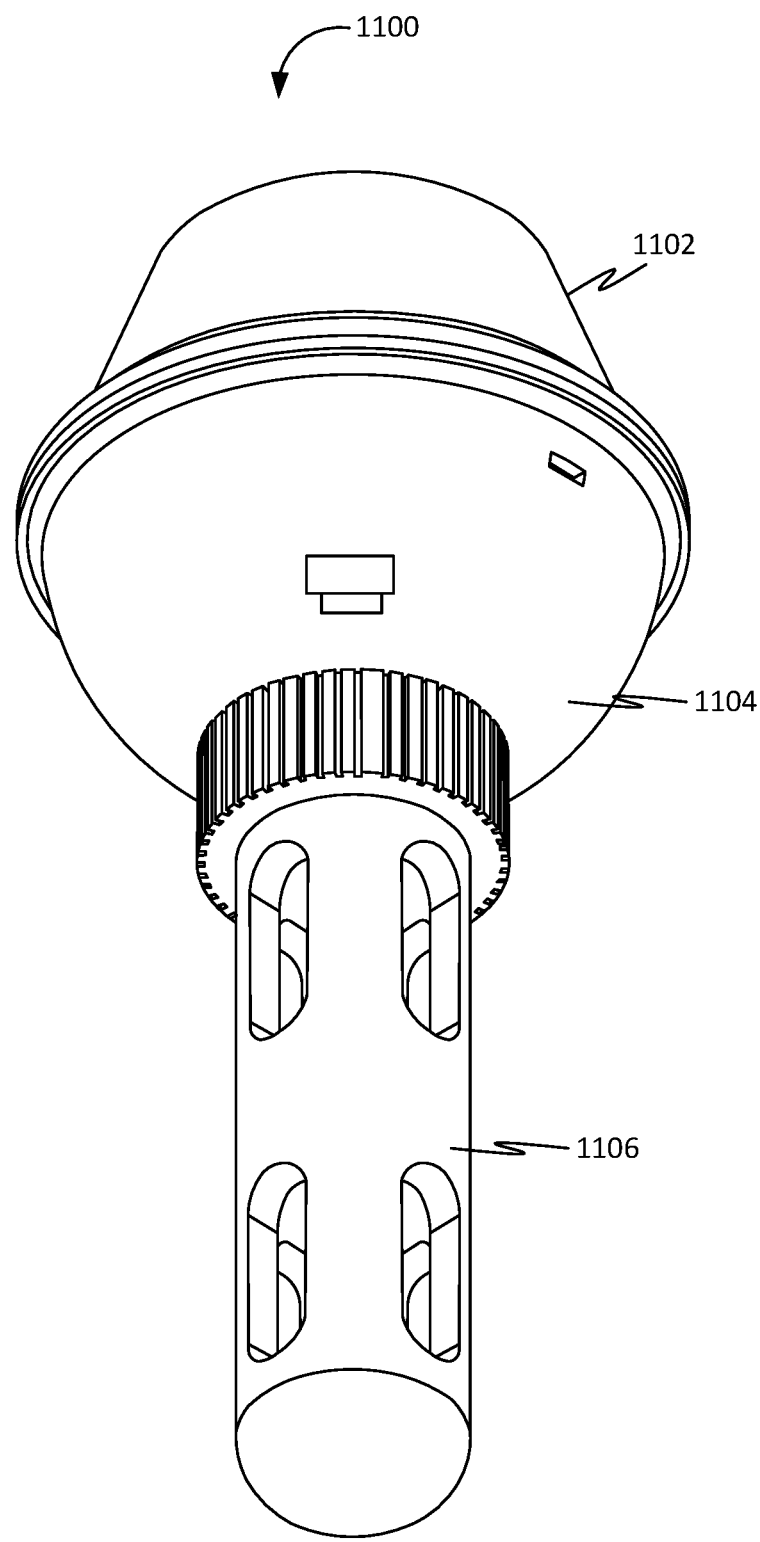
FIG. 12 is a bottom front perspective view of the apparatus, in accordance with some embodiments.

FIG. 12 is a bottom front perspective view of the apparatus 1100, in accordance with some embodiments.

Figure 13:
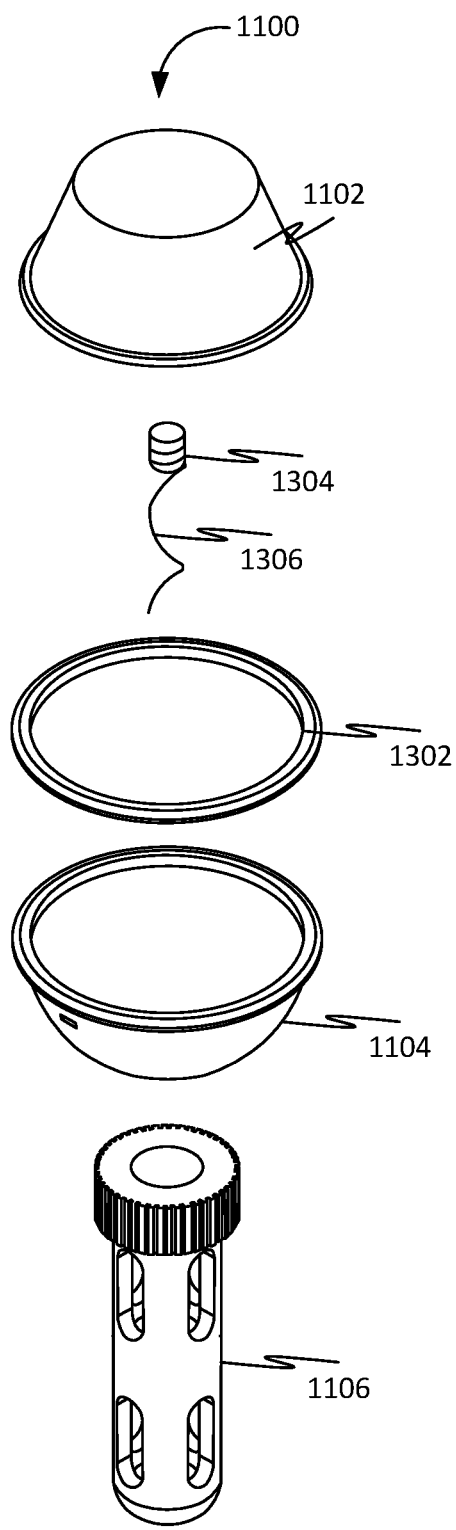
FIG. 13 is an exploded view of the apparatus, in accordance with some embodiments.

FIG. 13 is an exploded view of the apparatus 1100, in accordance with some embodiments.

Figure 14:
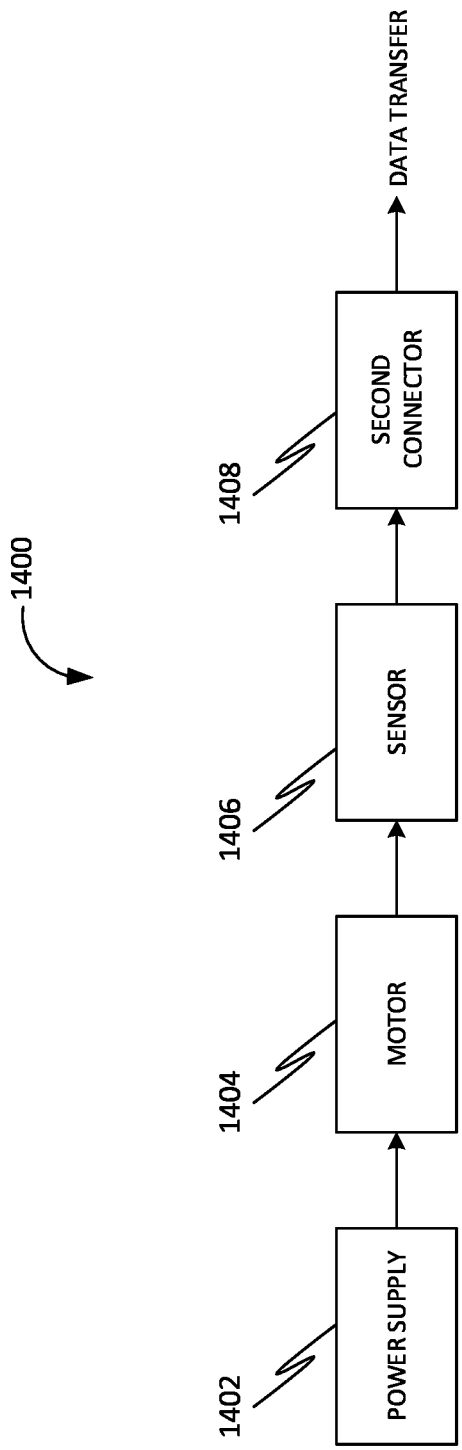
FIG. 14 is a block diagram of a system for facilitating sampling water of water bodies, in accordance with some embodiments.

FIG. 14 is a block diagram of a system 1400 for facilitating sampling water of water bodies, in accordance with some embodiments. Further, the system 1400 may include a power supply 1402, a motor 1404, a sensor 1406, and a second connector 1408. Further, the second connector 1408 allows data transfer.

Figure 15:
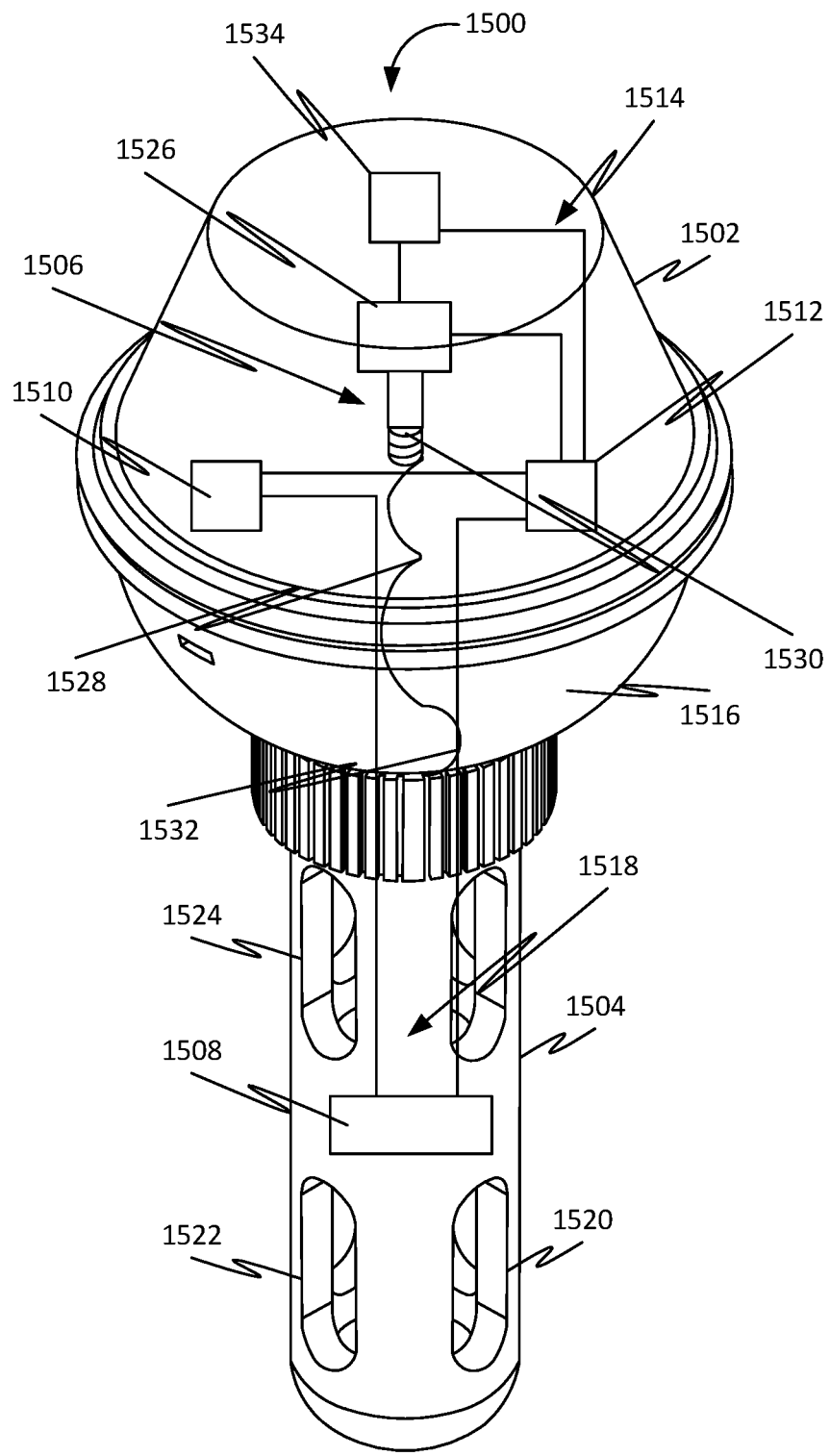
FIG. 15 is a top front perspective of an apparatus for facilitating sampling water of water bodies, in accordance with some embodiments.

FIG. 15 is a top front perspective of an apparatus 1500 for facilitating sampling water of water bodies, in accordance with some embodiments. Further, the apparatus 1500 may be disposable on a water surface of the water bodies. Further, the apparatus 1500 may include a primary housing 1502, a secondary housing 1504, a movement assembly 1506, at least one sensor 1508, a storage device 1510, a processing device 1534, and at least one power source 1512. Further, the primary housing 1502 may include a primary interior cavity 1514. Further, the primary housing 1502 may be disposable on at least one water surface of at least one water body. Further, the secondary housing 1504 may be movably disposed on a lower portion 1516 of the primary housing 1502. Further, the secondary housing 1504 may be submerged in the at least one water body based on disposing of the primary housing 1502 on the at least one water surface. Further, the secondary housing 1504 may include a secondary interior cavity 1518 and at least one opening 1520-1524 leading into the secondary interior cavity 1518. Further, the secondary housing 1504 may be transitionable between a retracted position and at least one extended position. Further, the secondary housing 1504 may be configured for receiving at least one water sample from at least one depth of the at least one water body in the secondary interior cavity 1518 through the at least one opening 1520-1524 based on submerging of the secondary housing 1504 in the at least one water body in the at least one depth. Further, the submerging of the secondary housing 1504 in the at least one depth may be based on transitioning of the secondary housing 1504 from the retracted position to the at least one extended position. Further, the movement assembly 1506 may be disposed in the primary interior cavity 1514 of the primary housing 1502. Further, the movement assembly 1506 may be operationally coupled with the secondary housing 1504.

Further, the movement assembly 1506 may be configured for transitioning the secondary housing 1504 between the retracted position and the at least one extended position. Further, the movement assembly 1506 may include at least one actuator 1526 and at least one tether 1528. Further, a first end 1530 of the at least one tether 1528 may be coupled with the at least one actuator 1526 and a second end 1532 of the at least one tether 1528 may be coupled with the secondary housing 1504. Further, the at least one actuator 1526 may be configured for transitioning the at least one tether 1528 between a retracted state and at least one extended state. Further, the transitioning of the secondary housing 1504 between the retracted position and the at least one extended position may be based on the transitioning the at least one tether 1528 between the retracted state and the at least one extended state. Further, the at least one sensor 1508 may be disposed in the secondary interior cavity 1518. Further, the at least one sensor 1508 may be configured for generating at least one sensor data based on detecting at least one characteristic of the at least one water sample received in the secondary interior cavity 1518. Further, the storage device 1510 may be disposed in the primary interior cavity 1514. Further, the storage device 1510 may be communicatively coupled with the at least one sensor 1508. Further, the storage device 1510 may be configured for storing the at least one sensor data. Further, the processing device 1534 may be disposed in the primary interior cavity 1514. Further, the processing device 1534 may be communicatively coupled with the at least one actuator 1526. Further, the processing device 1534 may be configured for analyzing at least one operational data. Further, the processing device 1534 may be configured for generating at least one command based on the analyzing of the at least one operational data. Further, the transitioning of the at least one tether 1528 between the retracted state and the at least one extended state may be based on the at least one command. Further, the at least one power source 1512 may be disposed in the primary interior cavity 1514. Further, the at least one power source 1512 may be electrically coupled with the at least one actuator 1526, the at least one sensor 1508, the storage device 1510, and the processing device 1534. Further, the at least one power source 1512 may be configured for powering the at least one actuator 1526, the at least one sensor 1508, the storage device 1510, and the processing device 1534.

Further, in some embodiments, the primary housing 1502 may be watertight.

Further, in some embodiments, the storage device 1510 may be further configured for storing the at least one operational data.

In further embodiments, the apparatus 1500 may include a communication device disposed in the primary interior cavity 1514. Further, the communication device may be electrically coupled with the at least one power source 1512. Further, the at least one power source 1512 may be further configured for powering the communication device. Further, the communication device may be communicatively coupled with the processing device 1534. Further, the communication device may be further configured for receiving the at least one operational data from at least one user device.

Further, in some embodiments, the primary housing 1502 may be configured to be flotably disposed on the at least one water surface of the at least one water body.

In further embodiments, the apparatus 1500 may include at least one communication interface disposed in the primary interior cavity 1514. Further, the at least one communication interface may be communicatively coupled with the storage device 1510. Further, the at least one communication interface may be configured for establishing a connection between the apparatus 1500 and at least one device. Further, the establishing of the connection allows transferring of the at least one sensor data from the storage device 1510 to the at least one device.

Figure 16:
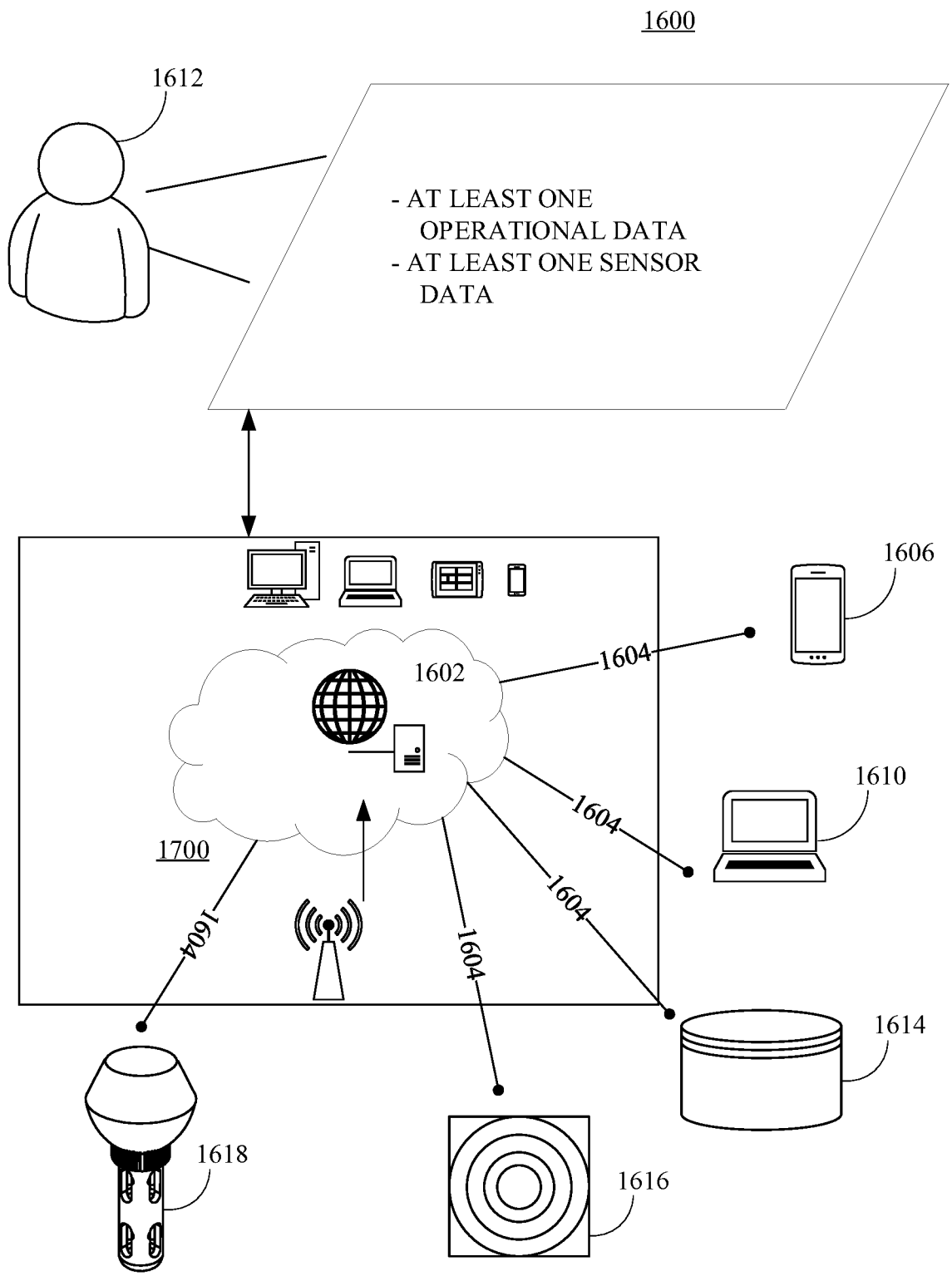
FIG. 16 is an illustration of an online platform consistent with various embodiments of the present disclosure.

FIG. 16 is an illustration of an online platform 1600 consistent with various embodiments of the present disclosure. By way of non-limiting example, the online platform 1600 to facilitate sampling water of water bodies may be hosted on a centralized server 1602, such as, for example, a cloud computing service. The centralized server 1602 may communicate with other network entities, such as, for example, a mobile device 1606 (such as a smartphone, a laptop, a tablet computer etc.), other electronic devices 1610 (such as desktop computers, server computers etc.), databases 1614, sensors 1616, and an apparatus 1618 (such as the apparatus 100, the apparatus 1100, the apparatus 1500, etc.) over a communication network 1604, such as, but not limited to, the Internet. Further, users of the online platform 1600 may include relevant parties such as, but not limited to, end-users, administrators, service providers, service consumers and so on. Accordingly, in some instances, electronic devices operated by the one or more relevant parties may be in communication with the platform.

A user 1612, such as the one or more relevant parties, may access online platform 1600 through a web based software application or browser. The web based software application may be embodied as, for example, but not be limited to, a website, a web application, a desktop application, and a mobile application compatible with a computing device 1700.

Figure 17:
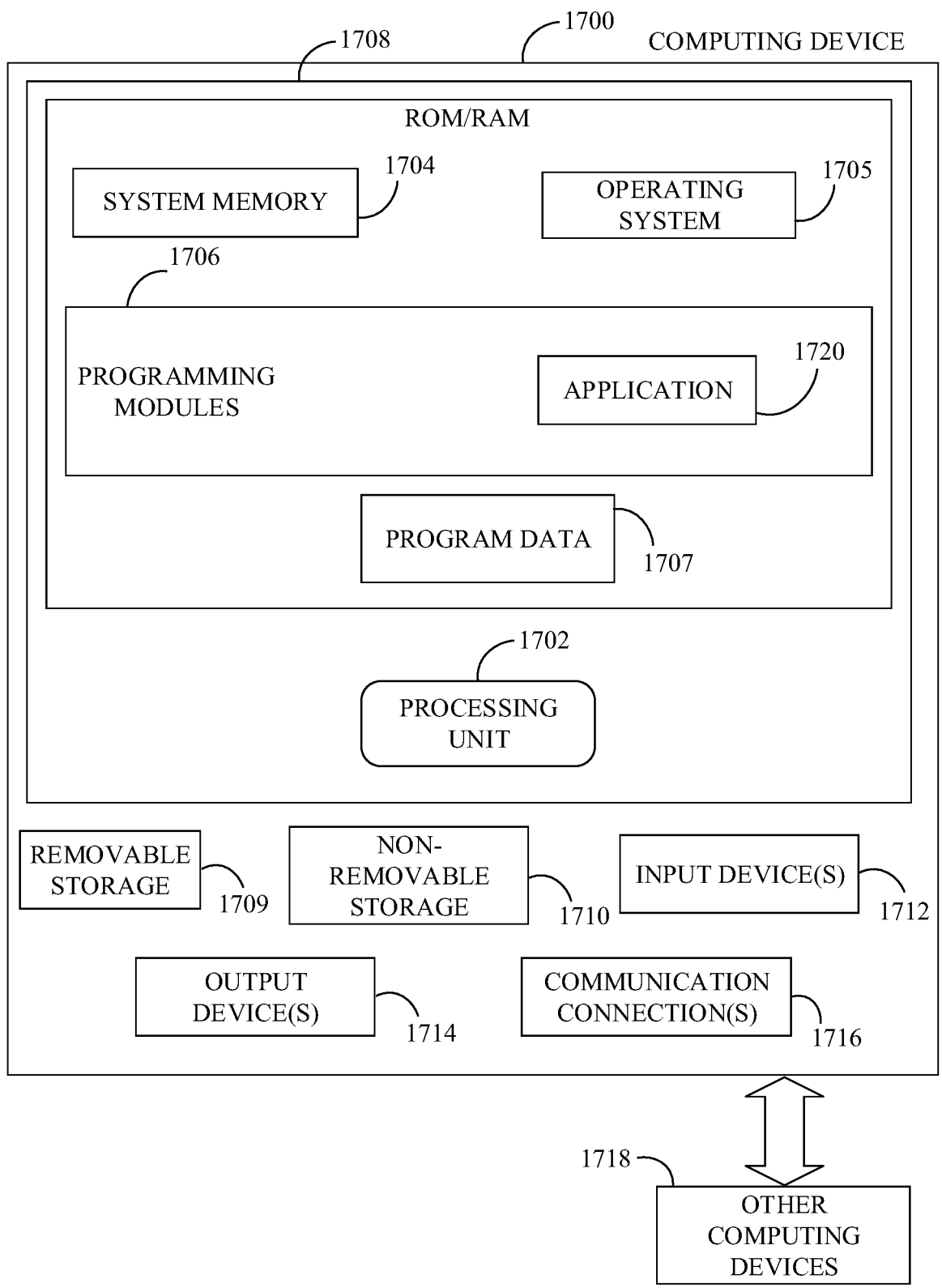
FIG. 17 is a block diagram of a computing device for implementing the methods disclosed herein, in accordance with some embodiments.

With reference to FIG. 17, a system consistent with an embodiment of the disclosure may include a computing device or cloud service, such as computing device 1700. In a basic configuration, computing device 1700 may include at least one processing unit 1702 and a system memory 1704. Depending on the configuration and type of computing device, system memory 1704 may comprise, but is not limited to, volatile (e.g., random-access memory (RAM)), non-volatile (e.g., read-only memory (ROM)), flash memory, or any combination. System memory 1704 may include operating system 1705, one or more programming modules 1706, and may include a program data 1707. Operating system 1705, for example, may be suitable for controlling computing device 1700's operation. In one embodiment, programming modules 1706 may include image-processing module, machine learning module. Furthermore, embodiments of the disclosure may be practiced in conjunction with a graphics library, other operating systems, or any other application program and is not limited to any particular application or system. This basic configuration is illustrated in FIG. 17 by those components within a dashed line 1708.

Computing device 1700 may have additional features or functionality. For example, computing device 1700 may also include additional data storage devices (removable and/or non-removable) such as, for example, magnetic disks, optical disks, or tape. Such additional storage is illustrated in FIG. 17 by a removable storage 1709 and a non-removable storage 1710. Computer storage media may include volatile and non-volatile, removable and non-removable media implemented in any method or technology for storage of information, such as computer-readable instructions, data structures, program modules, or other data. System memory 1704, removable storage 1709, and non-removable storage 1710 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1700. Any such computer storage media may be part of device 1700. Computing device 1700 may also have input device(s) 1712 such as a keyboard, a mouse, a pen, a sound input device, a touch input device, a location sensor, a camera, a biometric sensor, etc. Output device(s) 1714 such as a display, speakers, a printer, etc. may also be included. The aforementioned devices are examples and others may be used.

Computing device 1700 may also contain a communication connection 1716 that may allow device 1700 to communicate with other computing devices 1718, such as over a network in a distributed computing environment, for example, an intranet or the Internet. Communication connection 1716 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1704, including operating system 1705. While executing on processing unit 1702, programming modules 1706 may perform processes including, for example, one or more stages of methods, algorithms, systems, applications, servers, databases as described above. The aforementioned process is an example, and processing unit 1702 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. An apparatus for facilitating sampling water of water bodies, wherein the apparatus is disposable on a water surface of the water bodies, wherein the apparatus comprising:
   a primary housing comprising a primary interior cavity, wherein the primary housing is disposable on at least one water surface of at least one water body;
   a secondary housing movably disposed on a lower portion of the primary housing, wherein the secondary housing is submerged in the at least one water body based on disposing of the primary housing on the at least one water surface, wherein the secondary housing comprises a secondary interior cavity and at least one opening leading into the secondary interior cavity, wherein the secondary housing is transitionable between a retracted position and at least one extended position, wherein the secondary housing is configured for receiving at least one water sample from at least one depth of the at least one water body in the secondary interior cavity through the at least one opening based on submerging of the secondary housing in the at least one water body in the at least one depth, wherein the submerging of the secondary housing in the at least one depth is based on transitioning of the secondary housing from the retracted position to the at least one extended position;

a movement assembly disposed in the primary interior cavity of the primary housing, wherein the movement assembly is operationally coupled with the secondary housing, wherein the movement assembly is configured for transitioning the secondary housing between the retracted position and the at least one extended position, wherein the movement assembly comprises at least one actuator and at least one tether, wherein a first end of the at least one tether is coupled with the at least one actuator and a second end of the at least one tether is coupled with the secondary housing, wherein the at least one actuator is configured for transitioning the at least one tether between a retracted state and at least one extended state, wherein the transitioning of the secondary housing between the retracted position and the at least one extended position is based on the transitioning the at least one tether between the retracted state and the at least one extended state;

at least one sensor disposed in the secondary interior cavity, wherein the at least one sensor is configured for generating at least one sensor data based on detecting at least one characteristic of the at least one water sample received in the secondary interior cavity;

a storage device disposed in the primary interior cavity, wherein the storage device is communicatively coupled with the at least one sensor, wherein the storage device is configured for storing the at least one sensor data; and at least one power source disposed in the primary interior cavity, wherein the at least one power source is electrically coupled with the at least one actuator, the at least one sensor, and the storage device, wherein the at least one power source is configured for powering the at least one actuator, the at least one sensor, and the storage device.

2. The apparatus of claim 1, wherein the primary housing is watertight.

3. The apparatus of claim 1 further comprising a processing device disposed in the primary interior cavity, wherein the processing device is electrically coupled with the at least one power source, wherein the at least one power source is further configured for powering the processing device, wherein the processing device is communicatively coupled with the at least one actuator, wherein the processing device is configured for:
analyzing at least one operational data; and
generating at least one command based on the analyzing of the at least one operational data, wherein the transitioning of the at least one tether between the retracted state and the at least one extended state is based on the at least one command.

4. The apparatus of claim 3, wherein the storage device is further configured for storing the at least one operational data.

5. The apparatus of claim 3 further comprising a communication device disposed in the primary interior cavity, wherein the communication device is electrically coupled with the at least one power source, wherein the at least one power source is further configured for powering the communication device, wherein the communication device is communicatively coupled with the processing device, wherein the communication device is further configured for receiving the at least one operational data from at least one user device.

6. The apparatus of claim 1 further comprising a communication device disposed in the primary interior cavity, wherein the communication device is electrically coupled with the at least one power source, wherein the at least one power source is further configured for powering the communication device, wherein the communication device is communicatively coupled with the storage device, wherein the communication device is configured for transmitting the at least one sensor data to at least one user device.

7. The apparatus of claim 1, wherein the at least one actuator comprises a motor, wherein the movement assembly further comprises a wounding member, wherein a shaft of the motor is mechanically coupled with a first end of the wounding member, wherein the at least one tether is unwoundably woundable on the wounding member, wherein the motor is configured for rotating the wounding member in at least one of a clockwise direction and an anticlockwise direction about a longitudinal axis of the wounding member for unwoundingly wounding the at least one tether on the wounding member, wherein the transitioning of the at least one tether between the retracted state and the at least one extended state is based on the unwoundingly wounding the at least one tether on the wounding member.

8. The apparatus of claim 1 further comprises at least one connection element disposed on a top portion of the primary housing, wherein the at least one connection element is configured to be detachably attachable to at least one drone connection element of at least one drone for detachably attaching the apparatus to the at least one drone, wherein the at least one drone disposes the apparatus on the water surface.

9. The apparatus of claim 8, wherein the at least one drone maneuvers the apparatus on the water surface of the water bodies based on attaching of the apparatus to the at least one drone.

10. The apparatus of claim 9 further comprising at least one lighting device disposed on the primary housing, wherein the at least one lighting device is electrically coupled with the at least one power source, wherein the at least one power source is further configured for powering the at least one lighting device, wherein the at least one lighting device is configured for illuminating at least a portion of the water bodies, wherein the illuminating facilitates maneuvering of the apparatus.

11. The apparatus of claim 10, wherein the illuminating further comprises illuminating the at least one water sample, wherein the detecting of the at least one characteristic is further based on the illuminating of the at least one water sample.

12. The apparatus of claim 1 further comprising at least one communication interface disposed in the primary interior cavity, wherein the at least one communication interface is communicatively coupled with the storage device, wherein the at least one communication interface is configured for establishing a connection between the apparatus and at least one device, wherein the establishing of the connection allows transferring of the at least one sensor data from the storage device to the at least one device.

13. The apparatus of claim 1, wherein the primary housing is configured to be flotably disposed on the at least one water surface of the at least one water body.

14. The apparatus of claim 1 further comprising at least one activation sensor disposed on the primary housing, wherein the at least one activation sensor is coupled with the at least one power source, wherein the at least one activation sensor is configured for generating at least one activation signal based on detecting disposing of the apparatus on the water surface of the water bodies, wherein the powering of the at least one actuator, the at least one sensor, and the storage device is further based on the at least one activation signal.

* * * * *